United States Patent [19]
Tajima

[11] Patent Number: 6,100,079
[45] Date of Patent: Aug. 8, 2000

[54] METHOD FOR TREATING BIOPOLYMERS, MICROORGANISMS OR MATERIALS BY USING MORE THAN ONE TYPE OF MAGNETIC PARTICLES

[75] Inventor: Hideji Tajima, Inagi, Japan

[73] Assignee: Precision System Science Co., Ltd., Tokyo, Japan

[21] Appl. No.: 09/125,581

[22] PCT Filed: Feb. 24, 1997

[86] PCT No.: PCT/JP97/00515

§ 371 Date: Dec. 21, 1998

§ 102(e) Date: Dec. 21, 1998

[87] PCT Pub. No.: WO97/31105

PCT Pub. Date: Aug. 28, 1997

[30] Foreign Application Priority Data

Feb. 25, 1996 [JP] Japan ................................. 8-063816

[51] Int. Cl.[7] .............................. C12N 7/02; C12N 11/06; C07H 21/00
[52] U.S. Cl. .................. 435/239; 435/181; 435/820; 536/25.4
[58] Field of Search .................... 435/239, 181, 435/820; 536/25.4

[56] References Cited

FOREIGN PATENT DOCUMENTS

| | | |
|---|---|---|
| 6-294796 | 10/1994 | Japan . |
| 6-300754 | 10/1994 | Japan . |
| 6-510363 | 11/1994 | Japan . |
| 9-009957 | 1/1996 | Japan . |
| 8-029425 | 2/1996 | Japan . |
| 8-320274 | 12/1996 | Japan . |

*Primary Examiner*—Ali Salimi
*Attorney, Agent, or Firm*—Haynes and Boone, LLP

[57] ABSTRACT

Method and apparatus are described for purifying and separating biopolymers from a homogenized biological milieu using a pipette tip. The biopolymers are complexed with first magnetic particles. A magnet is applied to the pipette tip to attract the biopolymer/magnetic particle complex to the inner surface of the pipette tip adjacent to the magnet for separation from the biological milieu. The magnet is removed and the magnetic particles dissociated and removed from the biopolymers. Second magnetic particles are bound to the biopolymers. The magnet is replaced against the exterior surface of the pipette tip, thereby attracting the bound biopolymers to the inner surface of the pipette tip adjacent to the magnet to allow separation from impurities. The biopolymers are then labeled for detection, which may include detecting the concentration and identity of the biopolymer.

19 Claims, 1 Drawing Sheet

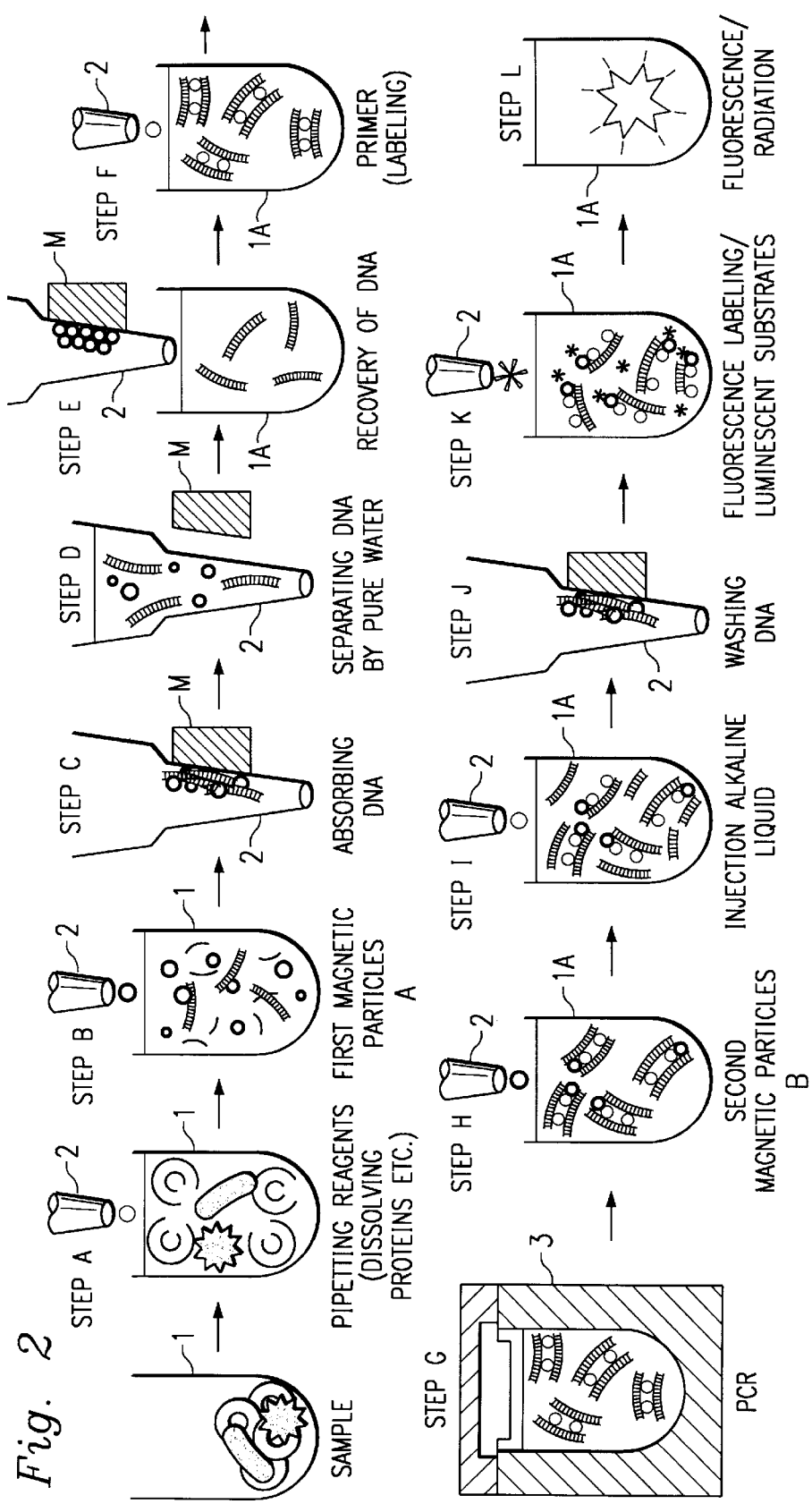

METHOD FOR TREATING BIOPOLYMERS, MICROORGANISMS OR MATERIALS BY USING MORE THAN ONE TYPE OF MAGNETIC PARTICLES

This application claims priority from PCT/JP97/00515, field Feb. 24, 1997.

FIELD OF THE INVENTION

The present invention relates to a method of processing biopolymers, microorganisms or substances, including DNA, RNA, mRNA, plasmid, viruses, bacteria and cells (all these are referred to as "DNA and the like") by using two or more kinds of magnetic particles, which enables automatic performance of processing, such as capture of cells, dissolution of cell nuclei and proteins, extraction and isolation of DNA and the like, and labeling, measuring or recovery of DNA and the like.

DESCRIPTION OF RELATED ART

In recent years, research on DNA and the like has been conducted in many fields such as engineering, medicine, agriculture, science and pharmacy, and its objectives range widely from genome sequencing, clinical diagnoses, breed improvement of agricultural plants, food bacillus inspection, and medicine development system.

Analysis of DNA and the like, whose application involves a wide range of fields and is expected to expand, has been performed in many ways, including centrifugal separation, high-performance liquid chromatography, gel electrophoresis, disposable column method, dialysis method, glass powder method, magnetic particle washing nozzle method, and immune serum reaction.

With the centrifugal separation method, however, loading and takeup of containers is very difficult to be automated and, after centrifugation, it is also very difficult to mechanically fractionate supernatants and precipitates. This method therefore lacks versatility.

With the high-performance liquid chromatography, because separation columns are essentially consumables, management of injection of samples into the columns and of separation time cannot be automated. Another problem with this method is that because samples are passed through the same column, contamination cannot be prevented completely.

In the case of the gel electrophoresis, adjustment of the gel cannot be automated and, although the DNA separation is a generally known as fundamental technique, there is no alternative but to use it manually to extract the separated fragments.

The disposable column method, one of methods that can be used as a kit to extract specific DNA fragments, is very costly and has a limited range of use. A further problem is the difficulty in controlling the pipetting of liquids and the amount of liquids supplied into columns, and many problems remain to be solved before automation can be realized.

The dialysis method takes time and has difficulty dealing with small amounts of samples and thus is not widely used.

The glass powder method is an excellent method of extracting DNA by using silicon dioxide. Although its process is simple, this method separates powder by filter or centrifugal separation and thus has a drawback of not being able to be automated easily.

The magnetic particle washing nozzle method, although it can be automated by controlling liquid suction and pouring by means of a cylinder and magnetic particles, has a problem that contamination basically cannot be eliminated by washing the nozzle.

The immune serum reaction is normally carried out by either a liquid phase method or a solid phase method. The liquid phase method has a similar problem to that experienced by the centrifugal separation. The solid phase method, too, has a problem similar to that of the centrifugal separation and requires many kinds of filters for separation from solid carriers, which makes the total automation difficult to realize. Another problem is that the use of many kinds of solid carriers makes this method difficult to handle and there is no appropriate means to avoid non-specific binding, giving rise to a limitation on highly sensitive and specific analyses.

The present invention has been accomplished under these situations and its objective is to first provide a method of processing DNA and the like, which, only by combining at least two kinds of magnetic particles, enables automatic and consistent performance of a series of processing including capture of cells, dissolution of cell nuclei and proteins, extraction and isolation of DNA and the like, and labeling and measuring of DNA and the like. A second objective is to provide an ideal method of processing DNA and the like, which can realize more efficient, fully automatic analysis of DNA and the like and guarantee thorough prevention of cross contamination by combining the principle of the first objective mentioned above with the principle of Japanese Patent Application No. H7-39425, "Magnetic Material Attracting/Releasing Control Method Making Use of a Pipette Device and Various Types of Analyzer using the Method," previously proposed by this applicant. A third objective is to provide a method of processing DNA and the like, which can carry out a series of processing including concentration, stirring, centrifugal separation and dialysis by controlling two or more kinds of magnetic particles and thereby reduce the equipment size and cost. A fourth objective is to provide a method of processing DNA and the like, which selectively uses from among a plurality of kinds of magnetic particles the optimum magnetic particles in each step of processing to execute a variety of processing, each consisting of many steps, highly efficiently, reliably, securely and swiftly and which is highly diversified and versatile.

DISCLOSURE OF THE INVENTION

To achieve the above objective, the processing method according to the first aspect of this invention comprises the steps of: automatically performing processes, including capture, extraction, recovery, isolation, amplification, labeling, analysis and measurement, on biopolymers, microorganisms or substances such as cells, DNA, RNA, mRNA, plasmid, viruses or bacteria by using two or more kinds of magnetic particles suited for the purposes of the processes.

The word "processes" include capture, extraction, recovery, isolation, amplification, labeling, analysis and measurement. The word "biopolymers" refer to polymeric substances synthesized in vivo, including proteins, nucleic acids (DNA, RNA, mRNA, etc.) and polysaccharide. Proteins include immunity substances. "Microorganisms" include viruses, plasmid, bacteria and cells. "Substances" include organic or inorganic chemical substances including molecular biological substances other than biopolymers. "Two or more kinds" refer to kinds of magnetic particles classified by size, shape, material, physical property, surface characteristic such as porosity, and bonding or binding substance or coating substance of magnetic particles.

A way to perform processes "by using two or more kinds of magnetic particles suited for the purposes of the processes" may involve binding the substance being processed to magnetic particles directly or indirectly through other substances, applying a magnetic field to the magnetic particles to separate the magnetic particles as by a pipette means and removing a residual liquid, or removing the magnetic particles themselves, or eliminating the magnetic field to suspend the magnetic particles in a liquid to capture the target substance, or dissociating the target substance, or performing a combination of these or repeating these steps. Thus, depending on the contents of the process, it is possible to remove the magnetic particles used in a preceding process and introduce new and the same magnetic particles.

The use of a plurality of kinds of magnetic particles allows an optimum kind of magnetic particles to be selected for each process. This not only enhances the efficiency and reliability of each process but enables automatic and consistent performance of a series of complex processes swiftly. Further, because unwanted residual substances from the preceding processes can be removed without washing, the processes can be performed with high precision and reliability.

A magnetic field may be applied to the magnetic particles, for example, from the outside of a liquid passage of a pipette means that connects the front end and the storage portion of the pipette means when a liquid suspended with the magnetic particles is drawn in or poured out through the liquid passage by the pumping action of the pipette means. This allows efficient separation of the magnetic particles from the liquid for further processing such as concentration, capture, extraction, recovery and isolation.

The word "automatically" refers to a manner in which processes are performed by specifying, according to the contents and sequence of processes, the suction and discharge actions of the pipette means and the number times such actions are to be performed, by locating the positions of containers containing samples and various kinds of magnetic particles, by specifying whether the used magnetic particles shall be discarded, where the containers are to be transported and whether a magnetic field is to be applied or not, and by giving necessary signals to a transfer pipette, a container transporting device and a magnet based on a programmed incubation time.

The processing method according to the second aspect of this invention is characterized in that, in the first aspect of the invention, the processes, including capture, extraction, recovery, isolation, amplification, labeling, analysis and measurement, performed on biopolymers, microorganisms or substances such as cells, DNA, RNA, mRNA, plasmid, viruses or bacteria are performed by using a pipette tip removably attached to the end of a pipette nozzle of a transfer pipette.

This allows efficient and swift performance of processes without causing cross-contamination nor without having to wash the pipette tip.

The processing method according to the third aspect of this invention is characterized in that, in the second aspect of the invention, the pipette tip transfers magnetic particles binding biopolymers, microorganisms or specific substances between processes such as capture, extraction, recovery, isolation, amplification, labeling, analysis and measurement by pumping a sample into or out of the pipette and moving a magnet toward or away from the pipette.

The word "binding" includes adhesion to magnetic particles, adsorption and bonding to a particular substance coated on the magnetic particles, or binding to the magnetic particles through reaction of reactive substances.

The processing method according to the fourth aspect of this invention comprises the steps of: binding biopolymers, microorganisms or substances such as cells, DNA, RNA, mRNA, plasmid, viruses or bacteria to one kind of magnetic particles by using a pipette tip removably attached to the front end of a pipette nozzle of a transfer pipette; performing purification, such as capturing of cells, dissolution of cell nuclei and dissolution of proteins, to extract DNA, RNA or mRNA; and isolating specific sequence fragments by other kind of magnetic particles coated with probes, biotin or streptavidin. The nucleic acid, the body of gene, has a structure in which a stranded compound sugar consisting of sugar and phosphoric acid is combined through a glycosidic linkage with heterocyclic compounds containing nitrogen which include thymine (T), cytosine (C), adenine (A) and guanine (G) as bases.

The processing method according to the fifth aspect of this invention is characterized in that, in the first to fourth aspects of this invention, the processes, such as capture, extraction, recovery, isolation, amplification, labeling, analysis and measurement, that are performed on biopolymers, microorganisms or substances such as cells, DNA, RNA, mRNA, plasmid, viruses or bacteria by using two or more kinds of magnetic particles, are performed through immune reactions or through specific affinity substances such as complementary DNA.

The processing method according to the sixth aspect of this invention is characterized in that, in the fourth aspect of this invention, a process of amplifying DNA, RNA or mRNA is inserted between the processes of capture, extraction or isolation that are performed, by using two or more kinds of magnetic particles, on biopolymers, microorganisms or substances such as cells, DNA, RNA, mRNA, plasmid, viruses or bacteria.

Here, "DNA, RNA or mRNA" includes sequence fragments that constitute these.

The processing method according to the seventh aspect of this invention is characterized in that, in the fourth to sixth aspects of this invention, after the process of capture, extraction or isolation, by using two or more kinds of magnetic particles, of biopolymers, microorganisms or substances such as cells, DNA, RNA, mRNA, plasmid, viruses or bacteria, the isolated biopolymers such as particular sequence fragments, microorganisms or substances are assayed by chemiluminescence, fluorescence or enzymatic coloring or by immune reactions.

The processing method according to the eighth aspect of this invention is characterized in that, in the fourth to sixth aspects of this invention, biopolymers, microorganisms or substances such as cells, DNA, RNA, mRNA, plasmid, viruses or bacteria are bound to magnetic particles by using a pipette tip removably attached to the front end of a pipette nozzle of a transfer pipette and are purified as by capturing cells, dissolving cell nuclei or proteins or by immune reactions to extract DNA, RNA or mRNA, then the extracted DNA, RNA or mRNA is amplified as required and isolated by using the pipette tip and other kind of magnetic particles coated with antibodies, probes, biotin or streptavidin, and then the isolated DNA, RAN or mRNA is assayed by chemiluminescence, fluorescence or enzymatic coloring to determine the presence or absence and the amount of the particular sequence fragments.

The processing method according to the ninth aspect of this invention comprises the steps of: mixing or stirring first magnetic particles in a sample by a pipette means to bind a target substance in the sample to the first magnetic particles to capture the target substance; separating by the pipette means the first magnetic particles that have captured the target substance and removing a residual liquid; mixing or stirring a dissociation liquid and the first magnetic particles to dissociate the target substance from the first magnetic particles; removing the first magnetic particles; mixing or stirring by the pipette means to bind the target substance to second magnetic particles to capture the target substance; and separating the second magnetic particles capturing the target substance by the pipette means.

The "target substance" includes biopolymers, microorganisms and substances.

Addition of processes other than those described in this invention is not excluded. For example, steps of processing or labeling the target substance may be added before or after the dissociation of the target substance. The target substance therefore can change as the process proceeds.

"Separation by a pipette means" may be performed, for example, by applying a magnetic field to the interior of the pipet means as the pipette means pumps in or out the sample, to attract the magnetic particles to the inside of the pipet means.

By sequentially using two or more kinds of magnetic particles, this invention eliminates various unwanted substances used in preceding steps before proceeding to the next step. This prevents reactions or measurements carried out in the next step from being affected by residual unwanted substances carried over from the previous steps and remaining on the magnetic particles, as they would be when the same magnetic particles continue to be used. It is therefore possible to perform processing with high sensitivity, precision and reliability.

Although this invention uses two kinds of magnetic particles, third or fourth magnetic particles may also be used by repeating the process using the two kinds of magnetic particles.

The processing method according to the tenth aspect of this invention is characterized in that, in the ninth aspect of this invention, the target substance is DNA and the like including sequence fragments, the first magnetic particles are porous in their surfaces, the dissociation liquid is pure water, and the second magnetic particles are coated or bound with probes, biotin or streptavidin, and that the method includes the steps of: mixing the DNA and the like dissociated from the first magnetic particles with primers by the pipette tip as required; amplifying the DNA and the like that have reacted with the primers by a PCR and then labeling them with biotin; binding the particular biotin-labeled DNA and the like to the second magnetic particles and separating them; and binding chemiluminescent or fluorescent, reaction substances to the separated DNA and the like for assay.

The processing method according to the eleventh aspect of this invention is characterized in that the sample is a body fluid such as serum, the target substance is a an antigen or antibody, and the first magnetic particles or the second magnetic particles are coated or bound with a substance that reacts specifically with the target substance directly or indirectly through one or more intermediate substances.

With these aspects of this invention described above, a series of processes, such as capturing of cells, dissolution of cell nuclei or proteins, extraction, isolation and labeling of DNA and the like, and measurement, can be carried out automatically and consistently simply by using at least two or more kinds of magnetic particles.

In each of the above aspects, the above-mentioned first principle of utilizing two or more kinds of magnetic particles can be combined with a principle, previously proposed by the inventor of this invention, that controls sample processing in a transfer pipette through manipulation of a magnetic material, to achieve a fully automatic assay of DNA and the like with increased efficiency and ensure complete prevention of contamination.

Further, with the above aspects of the invention, because processes including concentration, stirring, centrifugation and dialysis can be carried out continuously by controlling two or more kinds of magnetic particles, the mechanism and control become very simple, allowing substantial reduction in equipment scale and cost.

Furthermore, in each of the above aspects of the invention, an optimum kind of magnetic particles is chosen from among a plurality of kinds for each process so that various processes can be performed efficiently, reliably and swiftly, increasing versatility and widening the range of applicability.

BRIEF DESCRIPTION OF THE DRAWINGS

FIG. 1 is a block diagram showing the outline configuration of one embodiment of an extraction and analysis device for DNA and the like according to this invention; and FIG. 2 is a process flow showing a series of operation steps performed by the device.

BEST MODE FOR CARRYING OUT THE INVENTION

A first embodiment of this invention will be described by referring to the accompanying drawings.

FIG. 1 shows the configuration of a DNA analyzer that combines the principle that this applicant previously proposed with two kinds of magnetic particles. FIG. 2 schematically shows a series of operations performed by the DNA analyzer. In addition to DNA, this device can also be applied to the extraction and analysis of biopolymers, microorganisms and substances, such as RNA, mRNA, plasmid and virus, as target substances.

The DNA analyzer of this embodiment has an XYZ transfer mechanism that drives a pipette nozzle in vertical and horizontal directions. The pipette tip 2 removably attached to the front end of the pipette nozzle is controlled to perform a series of operations including sampling, pipetting of reagents, pouring of first magnetic particles, adsorbing of DNA, suction of pure water, capturing of DNA and pouring of primer, as shown in FIG. 2. The container into which the primer was poured is then heated in multiple stages by polymerase chain reaction (PCR) 3 to amplify the DNA. After the amplification of DNA, the pipette tip 2 pours second magnetic particles into the container, followed by injection of alkaline liquid, pumping in and out of DNA washing liquid, and performance of chemiluminescence, fluorescence or enzyme coloring reaction.

The first magnetic particles are uniform in their spherical shape and are as minuscule as 0.3–5 microns across. The magnetic particles are porous in their surfaces and often made of a material mixed with silica gel so that they can efficiently adhere to the surfaces of DNA and the like for recovery.

The second magnetic particles are used for volumetric determination and measurement. To capture specific sequence fragments, the surfaces of probes or magnetic particles are coated with biotin or streptavidin and DNA and the like are labeled with streptavidin or biotin to take advantage of high affinity between biotin and streptavidin.

The PCR 3 is a known technique and apparatus for amplification of DNA. For example, the sample may be heated to 96° C. and then cooled down to 40° C., after which it is again heated to 96° C. and cooled to 40° C., this process being repeated two or more times.

The analyzer that determines the presence or the amount of target sequence fragments in the sample based on chemiluminescence, fluorescence or enzyme coloring may be a known optical measuring device for small amount of light, such as photomultiplier (PMT) and spectrophotometer.

Next, the process of analyzing DNA by using the DNA analyzer of the above configuration will be described by referring to FIG. 2.

First, required reagents (SDS and protease) are pipetted into a homogenized sample to dissolve protein (step a).

Then, the first magnetic particles are added to the protein-dissolved sample to cause DNA and the like in the sample to attach to the first magnetic particles by physical adsorption to capture DNA and the like (step b).

Next, after a predetermined incubation, the sample in the container is pumped into the pipette tip 2. A magnet M, movable toward and away from the pipette tip 2, is attached to the outer surface of the pipette tip 2 to attract the first magnetic particles capturing DNA and the like to the inner surface of the pipette tip (step c).

Next, pure water as a dissociation liquid is drawn into the pipette tip to dissociate the DNA and the like from the first magnetic particles that are bound to the DNA and the like (step d). At this time, the magnet Al is driven to a position apart from the pipette tip 2 by such a distance that the sample drawn in is not affected by magnetism.

Then, the magnet M is again placed on the outer surface of the pipette tip 2 to attract only the first magnetic particles to the inner surface of the pipette tip 2. With the magnetic particles held to the inner surface of the pipette tip 2, the DNA and the like is separated from pure water to recover only the DNA and the like (step e). After this, the first magnetic particles are discarded.

Next, the pipette tip 2 mixes the separated DNA and the like with a primer (step f).

Then, the DNA and the like that have reacted with the primer are loaded into the PCR 3 where they are repetitively heated (to 96° C.) and cooled (to 40° C.) to specified temperatures to amplify the DNA (step g).

Next, the pipette tip 2 labels the DNA sample amplified by the PCR 3 with biotin and injects the second magnetic particles coated with streptavidin that has a high specific affinity for biotin (step h).

The pipette tip 2 then adds an alkaline liquid to the DNA sample (step i) and then draws in the alkalized DNA sample. The magnet M is used to attract the second magnetic particles to the inner surface of the pipette tip 2, after which water is drawn into and out of the pipette tip to wash the second magnetic particles to isolate a particular sequence fragment (step j).

Then, chemiluminescent or fluorescent substances or enzyme coloring substances are added to the isolated sequence fragment to bind to the DNA and the like or to particles adhering to DNA (step k). A known optical measuring apparatus for weak light, such as a photomultiplier or spectrophotometer, is used to detect the presence or absence of the target sequence fragment or measure the amount of that fragment (step 1).

As described above, this embodiment uses a porous material for the first magnetic particles to allow easy dissociation by pure water and selects for the second magnetic particles a material that efficiently arrests a target substance by strongly binding to it. It is therefore possible to efficiently dissociate the first magnetic particles to recover the target substance and perform measurement efficiently. By discarding the first magnetic particles and replacing them with the second magnetic particles, unwanted residual substances adhering to the first magnetic particles can be removed, enhancing the reliability of measurement.

Next, a second embodiment of this invention as applied to an immune serum reaction will be explained.

In the configuration of the first embodiment, this second embodiment uses an antigen instead of DNA and first antibody-binding magnetic particles in place of the first magnetic particles. The immune serum reaction in the second embodiment further involves the use of a second antibody without using the primer or PCR, a third antibody for labeling, a dissociation agent other than water, and second magnetic particles attached to or coated with a substance that specifically reacts with the labeled third antibody.

An example case of this embodiment as applied to the detection of a carcinoembryonic antigen (CEA) will be explained.

In the first step, the following reagents are pipetted from reagent tips into each plate hole of a first reaction microplate. They include 1) anti-DNP mouse antibody-binding magnetic particles (first anti-body) as the first magnetic particles, 2) DNP-and biotin-labeled anti-CEA mouse antibody (second antibody) containing DNP that specifically reacts with the anti-DNP mouse antibody, 3) anti-CEA mouse antibody (third antibody) labeled with ALP (alkaline phosphatase) that produces luminescence upon reaction with luminescent substrates, 4) DNP-lysine as a dissociation agent, and 5) streptavidin-binding magnetic particles as the second magnetic particles. The dissociation agents for the bonds formed by antigen-antibody reactions may use substances containing the same kind of antigen or antibody as the one to be dissociated.

In the second step, a serum sample is drawn into a reaction tip, from which it is poured into a reaction container. Then, the anti-DNAP mouse antibody-binding magnetic particles as the first magnetic particles (first antibody) and the DNP-and biotin-labeled anti-CEA mouse antibody as the second antibody are pipetted into the reaction container, in which they are mixed and stirred. After a predetermined period of incubation, the CEA antigen, a target substance present in the serum, rather than directly binding to the first magnetic particles, specifically combines with the DNP-and biotin-labeled anti-CEA mouse antibody, which specifically reacts with and binds to the anti-DNP mouse antibody of the first magnetic particles. Hence, the target CEA antigen binds through the second antibody to the first magnetic particles coated with the first antibody.

In the third step, after incubation, the magnet is set close to the side surface of the pipette tip to create a magnetic field inside the tip to attract the first magnetic particles capturing the CEA antigen to the inner surface of the pipette tip, with the remaining liquid removed. The separated first magnetic particles are mixed with the ALP-labeled anti-CEA mouse antibody. They are stirred and incubated to let the ALP-labeled anti-CEA mouse antibody specifically react with and bind to the CEA antigen, the target substance attached to the first magnetic particles.

In the fourth step, after incubation, the first magnetic particles capturing the CEA antigen and the ALP-labeled anti-CEA mouse antibody are held to the inner surface of the pipette tip by creating a magnetic field inside the tip. After the remaining liquid is removed, a DNP-lysine solution as a dissociation agent is drawn into the pipette tip to release from the first magnetic particles the aggregate of the CEA antigen, the ALP-labeled anti-CEA mouse antibody and the DNP- and biotin-labeled anti-CEA mouse antibody. After the first magnetic particles are separated and removed, the streptavidin-binding magnetic particles as the second magnetic particles are pipetted into the remaining liquid. They are mixed and stirred, and the biotin-labeled anti-CEA mouse antibody of the aggregate specifically reacts with streptavidin coated on the second magnetic particles, causing the aggregate to be arrested by the second magnetic particles.

In the fifth step, after incubation, the second magnetic particles capturing the aggregate are separated by producing a magnetic field in the pipette tip. After the remaining liquid is removed, a luminescent substrate AMPPD is added to cause the ALP-labeled anti-CEA mouse antibody forming the aggregate to illuminate. The amount of light produced is then measured to assay the CEA antigen.

As described above, with this embodiment, because a plurality of kinds of magnetic particles (in this case, two kinds) are used successively, it is possible to select the optimum magnetic particles in each process, thereby enhancing the efficiency of the processes and eliminating adverse effects on the processes. In the above, case, for example, the substance coated to the first magnetic particles is easily made to release the captured substance by a dissociation agent, while the second magnetic particles hold the captured substance by strongly binding to it. This not only improves the efficiency of measurement but eliminates adverse effects the coating substance of the first magnetic particles has on the subsequent operations. This embodiment also ensures easy and thorough elimination of various unwanted residual substances used in the preceding processes. All of these features combine to ensure highly sensitive and reliable performance of subsequent processes, such as measurement.

In the first embodiment, the biotin-labeled DNA is bound to the second magnetic particles coated with streptavidin. This invention is not limited to this application and may be applied, for example, to processing whereby the DNA assay is performed by hybridization using probe. It also possible to coat oligo dT on the magnetic particles and mix the coated magnetic particles into a liquid dissolved with an extracted RNA to capture an mRNA, from which a cDNA is synthesized using a reverse transcriptase. Furthermore, magnetic particles coated with streptavidin may be pipetted into a liquid of cDNA hybridized to the biotin-labeled mRNA in order to cause the biotin-labeled mRNA to bind to the magnetic particles. Then, by putting a magnet close to the pipette tip, it is possible to collect the hybridized cDNA captured by the magnetic particles.

While this embodiment has been described to use two kinds of magnetic particles in analyzing DNA and the like, it is also possible to use three or more kinds of magnetic particles for the assay. For example, in the first embodiment, when cells are to be extracted after a small piece cut from a living organism is homogenized, the third magnetic particles may be coated with ligands or receptors so that the cells can be extracted by means of the magnetic particles. Although the above examples have been applied mainly to the processing of biopolymers, this invention is not limited to these substances but can of course be applied to the processing of chemical substances including organic or inorganic ones.

What is claimed is:

1. A method of purifying and separating biopolymers from a homogenized biological milieu using a pipette tip and a container, comprising the steps of:

depositing the biological milieu in the container without immobilization of the biopolymers;

adding first magnetic particles to the biological milieu to complex with the biopolymers;

removing the biological milieu from the container with the pipette tip;

applying a magnetic field to the pipette tip, thereby attracting the biopolymer/magnetic particle complex to the inner surface of the pipette tip for separation from the biological milieu;

removing the magnetic field from the pipette tip;

dissociating and separating the magnetic particles from the biopolymers;

binding second magnetic particles to the biopolymers; and applying the magnetic field to the pipette tip, thereby attracting the bound biopolymers to the inner surface of the pipette tip to allow separation from impurities.

2. The method of claim 1 further comprising the step of:

labeling the biopolymers for detection.

3. The method of claim 2 further comprising the step of:

detecting the concentration of the biopolymer.

4. The method of claim 2 further comprising the step of:

detecting the identity of the biopolymer.

5. A method of purifying and separating DNA from a homogenized biological milieu using a pipette tip and a container, comprising the steps of:

depositing the biological milieu in the container without immobilization of the DNA;

adding reagents to the biological milieu;

adding first magnetic particles to the biological milieu, such that the first magnetic particles adsorb DNA;

removing the biological milieu from the container with the pipette tip;

applying a magnetic field to the pipette tip, thereby attracting the biopolymer/magnetic particle complex to the inner surface of the pipette tip for separation from the biological milieu;

removing the magnetic field from the pipette tip;

drawing water into the pipette tip to dissociate the magnetic particles from the DNA;

applying the magnetic field to the pipette tip, thereby attracting the magnetic particles to the inner surface of the pipette tip for separation from the DNA;

amplifying the DNA via the polymerase chain reaction (PCR);

labeling the DNA;

binding second magnetic particles to the DNA to form a DNA sample;

disassociating the DNA sample to single strands thereof; and applying the magnetic field to the pipette tip, thereby attracting the DNA sample to the inner surface of the pipette tip to allow separation from impurities.

6. The method of claim 5 further comprising the steps of:

washing the DNA sample with water; and labeling the DNA sample for detection.

7. The method of claim 6 further comprising the step of: detecting the concentration of the DNA sample.

8. The method of claim 6 further comprising the step of: detecting the sequence of the DNA sample.

9. A method of processing a target biopolymer in a sample liquid comprising the steps of:
   adding first magnetic particles to the sample liquid to bind the freely suspended target biopolymer;
   separating the first magnetic particles and bound target biopolymer from the sample liquid;
   dissociating the first magnetic particles from the target biopolymers using a dissociation liquid;
   removing the first magnetic particles;
   adding second magnetic particles to bind the target biopolymer; and
   collecting the second magnetic particles, thereby capturing the target biopolymer.

10. The method of claim 9 wherein the steps of adding, separating, removing, and collecting are performed by using a pipette tip removably attached a transfer pipette.

11. The method of claim 10 wherein the pipette tip performs the steps of separating, removing, and collecting by moving a magnet toward the pipette to create a magnetic field which attracts the magnetic particles.

12. The method of claim 9 wherein the target biopolymer is a nucleotide, including sequencing fragments, the first magnetic particles are porous in their surfaces, the dissociation liquid is a pure water, and the second magnetic particles are coated or bound with probes, the method further comprising the steps of:
   (i) mixing the nucleotide with primers after dissociation from the first magnetic particles;
   (ii) amplifying the primed nucleotide by PCR;
   (iii) labeling the amplified nucleotide with biotin;
   (iv) binding the nucleotide/biotin particles to magnetic particles for separation from unbound nucleotide; and
   (v) binding assay substances to the nucleotide/biotin particles for assay to determine the presence and amount of the particular sequence fragments.

13. The method of claim 9 wherein the target biopolymer is an immunoprotein suspended freely in a biological fluid, and at least one of the first magnetic particles and the second magnetic particles are coated with a substance that reacts specifically with the immunoprotein.

14. A method of processing a target nucleotide in a sample liquid comprising the steps of:
   adding first magnetic particles to the sample liquid to bind the freely suspended target nucleotide;
   separating the first magnetic particles and bound target nucleotide from the sample liquid with a magnet applied to a pipette tip;
   dissociating the first magnetic particles from the target nucleotide using a dissociation liquid;
   removing the first magnetic particles;
   adding second magnetic particles coated with probes to bind the target nucleotide, thereby isolating specific sequence fragments; and
   collecting the second magnetic particles, thereby capturing the target nucleotide.

15. The method of claim 14 wherein the probes are specific affinity substances.

16. The method of claim 14 further comprising the step of amplifying the target nucleotide by PCR.

17. The method of claim 14 further comprising the step of assaying the target nucleotide to determine the presence and amount of the particular sequence fragments.

18. The method of claim 14 further comprising the step of:
   (i) amplifying the target nucleotide by PCR; and
   (ii) assaying the target nucleotide to determine the presence and amount of the particular sequence fragments.

19. An apparatus for purifying and separating biopolymers from a homogenized biological milieu, comprising:
   a movable pipette tip;
   a container disposed under the pipette tip, wherein the biological milieu is placed in the container without immobilization of the biopolymers;
   means for selectively adding and removing first and second sets of magnetic particles for complexing with the biopolymers; and
   a magnet for creating a magnetic field in the pipette tip, thereby attracting the magnetic particle/biopolymer complexes to the inner surface of the pipette tip adjacent to the magnetic field.

* * * * *

UNITED STATES PATENT AND TRADEMARK OFFICE
CERTIFICATE OF CORRECTION

PATENT NO. : 6,100,079
DATED : August 8, 2000
INVENTOR(S) : Hideji Tajima

Page 1 of 1

It is certified that error appears in the above-identified patent and that said Letters Patent is hereby corrected as shown below:

<u>Column 7,</u>
Line 32, replace "A1" with -- M --

Signed and Sealed this

Twenty-sixth Day of February, 2002

Attest:

Attesting Officer

JAMES E. ROGAN
Director of the United States Patent and Trademark Office